United States Patent [19]

Desmurs et al.

[11] Patent Number: 4,853,153
[45] Date of Patent: Aug. 1, 1989

[54] STABILIZATION OF MIXTURES OF CHLORINATION OF PHENOL/CHLOROPHENOLS

[75] Inventors: Jean-Roger Desmurs, Saint-Symphorien d'Ozon; Serge Ratton, Villefontaine, both of France

[73] Assignee: Rhone-Poulenc Chimie, Courbevoie, France

[21] Appl. No.: 101,013

[22] Filed: Sep. 25, 1987

[30] Foreign Application Priority Data

Sep. 25, 1986 [FR] France .............................. 86 13555

[51] Int. Cl.⁴ .............................................. B66D 3/08
[52] U.S. Cl. ............................... 252/400.22; 252/397; 252/407

[58] Field of Search .................... 252/397, 400.22, 407

[56] References Cited

U.S. PATENT DOCUMENTS 3,088,917  5/1963  Friedman et al. .................. 252/182
4,351,969  9/1982  Bourdon ............................. 568/774

*Primary Examiner*—A. Lionel Clingman
*Assistant Examiner*—Willie Thompson
*Attorney, Agent, or Firm*—Burns, Doane, Swecker & Mathis

[57] ABSTRACT

Mixtures produced by chlorination of phenol/chlorophenols are effectively stabilized by stirring same in the presence of a stabilizing amount of at least one reducing compound that is a chlorine acceptor.

26 Claims, No Drawings

STABILIZATION OF MIXTURES OF CHLORINATION OF PHENOL/CHLOROPHENOLS

CROSS-REFERENCE TO RELATED APPLICATIONS

Our copending applications, Ser. No. 100,783 and Ser. No. 100,844, filed concurrently herewith and assigned to the assignee hereof.

BACKGROUND OF THE INVENTION

1. Field of the Invention

The present invention relates to the stabilization of reaction mixtures produced during the chlorination of phenol and/or chlorophenols into tri-, tetra- and pentachlorophenols.

2. Description of the Prior Art

During the chlorination of phenol, monochlorophenols and dichlorophenols to produce trichlorophenols, tetrachlorophenols or pentachlorophenol, chlorination mixtures are obtained which are colored and which change upon the passage of time. Thus, even during cold storage, an increase in the level of chlorophenoxyphenols and a change in the concentration of certain of the chlorophenols are observed, in particular.

When such chlorination mixtures are distilled, the distillation products also reflect this instability.

In these chlorination mixtures, the present applicants have now determined that the presence of unsaturated cyclic ketones containing a gem-dichloro substituent appear to be the source of the change, or instability, in these mixtures.

SUMMARY OF THE INVENTION

Accordingly, a major object of the present invention is the provision of improved means for avoiding the problem of instability of chlorination mixtures of the aforesaid type.

Briefly, the present invention features the stabilization of reaction mixtures produced via the chlorination of phenol and/or chlorophenols, by stirring such mixtures in the presence of an effective stabilizing amount of at least one reducing compound that is a chlorine acceptor.

DETAILED DESCRIPTION OF THE PREFERRED EMBODIMENTS OF THE INVENTION

More particularly according to the present invention, the reducing compounds that are chlorine acceptors and useful herein are many and very widely varied.

Exemplary of the reducing compounds that are chlorine acceptors, representative are, in particular: organic phosphites; phosphines, phosphinates; arsines; organic sulfides, metal hydrides; metal borohydrides or derivatives of these metal borohydrides such as cyanoborohydrides or alkoxyborohydrides; certain metals such as copper, tin, silver, cobalt, palladium, platinum, iridium, germanium and selenium, or derivatives of certain of these metals; or phenols, diphenols or triphenols.

Among these reducing compounds that are chlorine acceptors, different classes may be distinguished.

The first, especially advantageous class comprises, in particular, trivalent phosphorus compounds of the general formula (I):

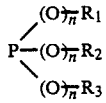

in which $R_1$, $R_2$ and $R_3$, which may be identical or different, are each a linear or branched chain alkyl radical having from 1 to 12 carbon atoms; a linear or branched chain alkyl radical having from 1 to 12 carbon atoms and containing one or more chlorine atoms; an alkyl radical containing one or more ether groups, such as, in particular, one or more ethylene oxide and/or propylene oxide sequences; a phenyl radical; a phenyl radical containing one or more chlorine atoms; a phenyl radical containing 1 or 2 alkyl substituents having from 1 to 12 carbon atoms; a phenylalkyl radical, the aliphatic moiety of which contains from 1 to 4 carbon atoms and in which the cyclic member can contain one or more chlorine atoms or 1 or 2 alkyl radicals having from 1 to 12 carbon atoms; or a cycloalkyl radical, in particular cyclohexyl, optionally substituted with one or more chlorine atoms or 1 or 2 alkyl radicals having from 1 to 12 carbon atoms; with the proviso that one or two of the radicals $R_1$, $R_2$ and $R_3$ can be a hydrogen atom; and the symbols n, which may be identical or different, are 0 or 1.

Exemplary of compounds of the formula (I), representative are triphenyl phosphite, tris(chlorophenyl) phosphites, tris(dichlorophenyl) phosphites, tris(trichlorophenyl) phosphites, trimethyl phosphite, triethyl phosphite, tributyl phosphite, trioctyl phosphite, tris(nonylphenyl) phosphites, tris(2,4-di-tert-butylphenyl) phosphite, tribenzyl phosphite, tris(phenethyl) phosphite, methyl diphenylphosphinate, tris(2-ethoxyethyl) phosphite, tricyclohexyl phosphite, triphenylphosphine, diphenylmethylphosphine, diphenylethylphosphine, diethylphenylphosphine and tributylphosphine.

This first class of reducing compounds that are chlorine acceptors also includes the arsines such as, for example: triphenylarsine, triphenylarsines substituted with one or more chlorine atoms or 1 or 2 alkyl groups having from 1 to 12 carbon atoms; trialkylarsines, the alkyl moieties of which have from 1 to 12 carbon atoms and can optionally be substituted with chlorine atoms; alkylphenylarsines such as diphenylethylarsine; and arsenites such as triethyl arsenite.

Finally, in this first class of reducing compounds that are chlorine acceptors, organic sulfides, thiols, mercapto acids and thiocarboxylic acids are also included because of their similarity in behavior.

These organic sulfides are more especially the compounds of the general formula (II):

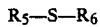

in which $R_5$ and $R_6$, which may be identical or different, are each a phenyl radical optionally substituted with one or more alkyl, alkoxy or hydroxyl radicals or chlorine atoms; an alkyl radical; a phenylalkyl radical optionally substituted with one or more alkyl, alkoxy or hydroxyl radicals or chlorine atoms; or a cyclopentyl or cyclohexyl radical optionally substituted with one or more alkyl, alkoxy or hydroxyl radicals or chlorine atoms.

Exemplary of such organic sulfides, representative are thioanisole, diphenyl sulfide, phenyl 4-chlorophenyl sulfide, bis(4-chlorophenyl) sulfide, bis(2-hydroxy-4,6-di-tert-butylphenyl) sulfide, bis(4-hydroxy-3,5-dimethylphenyl) sulfide, bis(2-hydroxy-3,5-di-tert-butylphenyl) sulfide, phenyl cyclohexyl sulfide, phenyl butyl sulfide, 4-chlorophenyl hexyl sulfide, 4-methylphenyl dodecyl sulfide, benzyl octyl sulfide, 4-methoxyphenyl ethyl sulfide, phenyl stearyl sulfide, dihexyl sulfide, ethyl hexyl sulfide, dioctyl sulfide, propyl 4-methylcyclohexyl sulfide and methyl 4-chlorocyclohexyl sulfide.

Thioanisole is a reducing compound that is a chlorine acceptor which is especially effective in the process according to the present invention.

Thiols, mercapto acids and thiocarboxylic acids are known compounds. Compare, for example, the chapters devoted to such compounds in Kirk-Othmer, *Encylopedia of Chemical Technology*, 3rd edition, Volume 22, pages 946 to 964, or in Houben-Weyl, *Methoden der Organischen Chemie*, Volume IX, page 746 et seq (1955).

Representative are, more especially, the compounds of the general formula (III):

$$R_7\text{—SH} \quad\quad (III)$$

in which $R_7$ is a linear or branched chain alkyl radical optionally substituted with one or more OH groups, —COOH groups or chlorine atoms and optionally containing in their chain one or more oxygen atoms —O—; a phenyl radical optionally substituted with one or more alkyl, alkoxy, hydroxyl or carboxyl radicals or chlorine atoms; a phenylalkyl radical optionally substituted with one or more alkyl, alkoxy, hydroxyl or carboxyl radicals or chlorine atoms; a cyclopentyl or cyclohexyl radical optionally substituted with one or more alkyl, alkoxy, hydroxyl or carboxyl radicals or chlorine atoms; or a radical $R_7$—CO—, in which $R_7$ is as defined above.

Exemplary of such thiols, mercapto acids or thiocarboxylic acids, representative are 2-mercaptoethanol, 3,4-toluenedithiol, 2-methyl-2-propanethiol, thiophenol, thioacetic acid, thioglycolic acid and 2-mercaptosuccinic acid.

The reducing compounds that are chlorine acceptors of this first class enable the mixtures that are produced in the chlorination of phenol and/or chlorophenols to be stabilized by converting all or a fraction of the gem-dichlorinated unsaturated cyclic ketones principally to chlorophenols, and only to a small extent, or not at all, to chlorophenoxyphenols.

A second active class of reducing compounds that are chlorine acceptors comprises metal hydrides, in particular those of the alkali metals, of alkaline earth metals or of aluminum and alkali metals, and alkali metal borohydrides or derivatives of alkali metal borohydrides such as cyanoborohydrides and alkoxyborohydrides.

Representative are, for example, sodium hydride, potassium hydride, lithium hydride, calcium hydride, magnesium hydride, lithium aluminum hydride, sodium borohydride, potassium borohydride, sodium cyanoborohydride, potassium cyanoborohydride, sodium trimethoxyborohydride, sodium triethoxyborohydride, potassium trimethoxyborohydride, potassium triethoxyborohydride and sodium dimethoxyborohydride.

This second class of reducing compounds that are chlorine acceptors also includes certain metals such as palladium, platinum, iridium, cobalt, copper, tin and silver, in their metallic form.

It also includes derivatives of certain of these metals, generally in their low oxidation state, in particular salts which are compatible with the reaction medium.

Representative are, for example, ruthenium trichloride and stannous chloride.

The reducing compounds that are chlorine acceptors of this second class enable the mixtures that are produced in the chlorination of phenol and/or chlorophenols to be stabilized by converting a fraction of the gem-dichlorinated unsaturated cyclic ketones to chlorophenols and another fraction of these ketones to chlorophenoxyphenols.

A third class of reducing compounds that are chlorine acceptors comprises phenols, diphenols and triphenols whether or not containing one or more alkyl or alkoxy substituents. These alkyl or alkoxy substituents have from 1 to 4 carbon atoms.

Exemplary are, for example, phenol, 2-methylphenol, 3-methylphenol, 4-methylphenol, 2-methoxyphenol, 3-methoxyphenol, 4-methoxyphenol, 2-ethoxyphenol, 3-ethoxyphenol, 4-ethoxyphenol, 4-tert-butylphenol, pyrocatechol, resorcinol, hydroquinone, 2-methylhydroquinone, 2-methoxyhydroquinone, 4-methoxypyrocatechol, 2,6-dimethoxyhydroquinone, 1-naphthol, 2-naphthol, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, pyrogallol, phloroglucinol, hydroxyquinol, 2-chlorohydroquinone and vitamin E.

The reducing compounds that are chlorine acceptors of this third class enable the mixtures that are produced in the chlorination of phenol and/or chlorophenols to be stabilized either by converting the gem-dichlorinated unsaturated cyclic ketones to chlorophenols, or by reacting with the cyclic ketones to produce heavy compounds of the chlorinated biphenyl or phenoxyphenol type.

One embodiment of the subject process comprises adding compounds such as, for example, phosphorus trichloride, phosphorous acid or hypophosphorous acid to the mixture that is produced in the chlorination of phenol and/or chlorophenols, which phosphorus compounds will form, in situ, with the chlorophenols present, chlorinated phenyl phosphites such as those described as belonging to the first class of reducing compounds that are chlorine acceptors.

These phosphorus compounds can also be added to the mixture to be treated, with one or more phenols of the third class of reducing compounds that are chlorine acceptors.

The gem-dichlorinated unsaturated cyclic ketones are principally gem-dichlorinated cyclohexadienones incidentally containing 1, 2, 3 or 4 other chlorine atoms on different carbon atoms of the ring, and gem-dichlorinated cyclohexenones also incidentally containing 1 to 6 other chlorine atoms on different carbon atoms of the ring.

These are, on the one hand, 4,4-dichloro-2,5-cyclohexadienones and 6,6-dichloro-2,4-cyclohexadienones containing, in addition, 1 to 4 chlorine atoms.

Exemplary of such principal gem-dichlorinated cyclohexadienones, representative are:
6,6-dichloro-2,4-cyclohexadienone,
4,4-dichloro-2,5-cyclohexadienone,
2,4,4,6-tetrachloro-2,5-cyclohexadienone,
2,4,6,6-tetrachloro-2,4-cyclohexadienone, 2,3,4,4,6-pentachloro-2,5-cyclohexadienone,
2,4,5,6,6-pentachloro-2,4-cyclohexadienone,
2,3,4,6,6-pentachloro-2,4-cyclohexadienone,
2,3,4,4,5,6-hexachloro-2,5-cyclohexadienone, and
2,3,4,5,6,6-hexachloro-2,4-cyclohexadienone.

These are, on the other hand, 2,2-dichloro-3-cyclohexenones, 6,6-dichloro-2-cyclohexenones, 4,4-dichloro-2-cyclohexenones and 6,6-dichloro-3-cyclohexenones containing, in addition, 1 to 6 chlorine atoms.

Exemplary of the principal gem-dichlorinated cyclohexenones, representative are:
2,4,5,6,6-pentachloro-2-cyclohexenone,
2,4,4,5,6,6-hexachloro-2-cyclohexenone,
2,2,4,5,6,6-hexachloro-3-cyclohexenone,
2,4,4,5,5,6,6-heptachloro-2-cyclohexenone,
2,2,3,4,5,6,6-heptachloro-3-cyclohexenone,
2,3,4,4,5,5,6-heptachloro-2-cyclohexenone,
2,3,4,4,5,6,6-heptachloro-2-cyclohexenone,
2,3,4,4,5,5,6,6-octachloro-2-cyclohexenone, and
2,2,3,4,5,5,6,6-octachloro-3-cyclohexenone.

The temperature at which the mixture that is produced by the chlorination of phenol and/or chlorophenols and the reducing compound or compounds that are chlorine acceptors is stirred varies oer wide limits, for example, from 20° C. to 200° C.

Preferably, however, in order to effect good reaction, the temperature will range from 40° C. to 180° C. and more preferably from 60° C. to 150° C.

The duration of the treatment is highly variable depending upon the temperature, the amount of gem-dichlorinated cyclic ketones present in the mixture and the reducing compound used that is a chlorine acceptor. It may vary, for example, from a few minutes to several tens of hours.

In general, it ranges from 1 hour to 15 hours, although these figures are not of critical importance.

The amount of reducing compound that is a chlorine acceptor depends, quite obviously, on the content of gem-chlorinated cyclic ketones in the mixture and on the nature of which. These ketones are generally assayed in the mixture by liquid chormatography via double detection: an ultraviolet detector for all of the compounds in the mixture collectively and an electrochemical detector specifically for the gem-dichlorinated cyclic ketones; or by an overall assay using electrochemistry.

To attain good stabilization of the chlorination mixtures, it is necessary to introduce a molar amount of reducing compound that is a chlorine acceptor which is at least equal to the molar amount of the gem-dichlorinated cyclic ketones.

Since it is not always easy to determine accurately the nature of the different gem-dichlorinated unsaturated cyclic ketones in the chlorination mixtures, it is preferable to introduce a molar excess of the reducing compound that is a chlorine acceptor.

In order to further illustrate the present invention and the advantages thereof, the following specific examples are given, it being understood that same are intended only as illustrative and in nowise limitative.

EXAMPLES 1 TO 6

A 10-cm$^3$ glass reactor equipped with a stirrer was charged with the following materials:
(i) 2,4,6-trichlorophenol: 1.97 g (0.010 mole);
(ii) 2,4,4,6-tetrachloro-2,5-cyclohexadienone: 0.23 g (0.001 mole);
(iii) reducing compound that is a chlorine acceptor: 0.0025 mole.

The mixture was heated under stirring for 8 hours at 75° C.

The reaction mass wa analyzed by liquid chromatography, using double detection with UV (totality of the chlorinated compounds) and amperometry (gem-dichlorinated unsaturated cyclic ketones).

Under the same conditions, a control experiment was carried out employing the same charges, except for the reducing compound that is a chlorine acceptor.

Table I below reflects the nature and amount of reducing compound that is a chlorine acceptor used, as well as the results of the analyses performed after the treatment.

TABLE I

| EXPERIMENT | Reducing chlorine acceptor weight in grams | % DC of the chlorocyclo-hexadienone phenol | % YLD of 2,3,4,6-tetrachloro-phenol | Weight of 4,6-DPP in g | Weight of 2,6-DPP in g |
|---|---|---|---|---|---|
| Control A | None | 4.8 | 19.8 | $3.52 \times 10^{-2}$ | $2.2 \times 10^{-2}$ |
| Example 1 | Triphenyl phosphite: 0.77 | 100 | 1.15 | 0 | 0 |
| Example 2 | Triphenylphosphine: 0.65 | 100 | 1.30 | 0 | 0 |
| Example 3 | Li Al hydride: 0.09 | 94.0 | 8.4 | $9.62 \times 10^{-2}$ | $8.24 \times 10^{-2}$ |
| Example 4 | Na borohydride: 0.09 | 86.1 | 0.75 | $2.3 \times 10^{-2}$ | $1.37 \times 10^{-2}$ |
| Example 5 | Copper metal: 0.16 | 100 | 0.70 | $10.86 \times 10^{-2}$ | $10.3 \times 10^{-2}$ |
| Example 6 | Stannous chloride: 0.47 | 99.6 | 0 | $2.7 \times 10^{-2}$ | $15.2 \times 10^{-2}$ |

DC = degree of conversion;
YLD = yield with respect to the chlorocyclohexadienone converted;
4,6-DPP = 4,6-Dichloro-2-(2,4,6-trichlorophenoxy)phenol;
2,6-DPP = 2,6-Dichloro-4-(2,4,6-trichlorophenoxy)phenol.

EXAMPLES 7 TO 9

A 10-cm$^3$ glass reactor equipped with a stirrer was charged with the following materials:
(i) 2,4,6-trichlorophenol: 1.97 g (0.010 mole);
(ii) 2,3,4,4,5,6-hexachloro-2,5-cyclohexadienone: 0.30 g (0.001 mole);
(iii) reducing compound that is a chlorine acceptor: 0.0025 mole.

The procedure was as in Examples 1 to 6: 8 hours at 75° C.

Table II below reflects the nature and amount of the reducing compound that is a chlorine acceptor used, as well as the results of the analyses performed after the treatment.

TABLE III

| EXAMPLES | Reducing chlorine acceptor Weight in grams | % DC of the chlorocyclo-hexadienone | % YLD of 2,3,4,6-tetrachloro-phenol | Weight of 4,6-DPP in g | Weight of 2,6-DPP in g |
|---|---|---|---|---|---|
| Example 10 | Phenol: 0.24 | 100 | 0 | 0 | 0 |
| Example 11 | Thioanisole: 0.31 | 100 | 0 | 0 | 0 |
| Example 12 | Resorcinol: 0.27 | 100 | 0 | 0 | 0 |
| Example 13 | Hydroquinone: 0.27 | 100 | 0 | 0 | 0 |
| Example 14 | Pyrocatechol: 0.27 | 100 | 0 | 0 | 0 |
| Example 15 | Pyrogallol: 9.31 | 100 | 0.2 | 0 | 0 |
| Example 16 | 2-Chlorohydroquinone: 0.38 | 98.0 | 0 | 0 | 0 |
| Example 17 | $RuCl_3$: 0.52 | 70.0 | 0 | 0 | 0 |
| Example 18 | Vitamin E: 0.115 | 100 | 0 | 0 | 0 |
| Example 19 | Trimethylhydroquinone: 0.38 | 100 | 0 | 0 | 0 |

DC = degree of conversion;
YLD = yield with respect to the chlorocyclohexadienone converted;
4,6-DPP = 4,6-Dichloro-2-(2,4,6-trichlorophenoxy)phenol;
2,6-DPP = 2,6-Dichloro-4-(2,4,6-trichlorophenoxy)phenol.

well as the results of the analyses performed after the treatment.

TABLE II

| Experiment | Reducing chlorine acceptor Weight in grams | % DC of the hexachloro-cyclohexa-dienone | % YLD of penta-chloro-phenol | Weight of CCPP in g | Weight of TCCD |
|---|---|---|---|---|---|
| Control B | None | 4.9 | 0 | 0 | 0 |
| Example 7 | Phenyl phosphite: 0.77 | 100 | 100 | $0.45 \times 10^{-2}$ | 0 |
| Example 8 | Triphenylphosphine: 0.66 | 100 | 100 | 0 | 0 |
| Example 9 | Tributylphosphine: 0.51 | 61.0 | 84.9 | $2.06 \times 10^{-2}$ | $2.39 \times 10^{-2}$ |

CCPP = mixture of chloro(chlorophenoxy)phenols
TCCD = 2,4,4,6-tetrachloro-2,5-cyclohexadienone.

EXAMPLES 10 TO 19

A 10-cm$^3$ glass reactor equipped with a stirrer was charged with the following materials:
(i) 2,4,6-trichlorophenol: 1.97 g (0.010 mole);
(ii) 2,4,4,6-tetrachloro-2,5-cyclohexadienone: 0.23 g (0.001 mole);
(iii) reducing compound that is a chlorine acceptor: 0.0025 mole.

The mixture was heated under stirring for 8 hours at 75° C.

The reaction mass was analyzed by liquid chromatography using a double detection with UV (totality of the chlorinated compounds) and amperometry (gem-dichlorinated unsaturated cyclic ketones).

Table III below reflects the nature and amount of the reducing compound that is a chlorine acceptor used, as well as the results of the analyses performed after the treatment.

EXAMPLES 20 TO 24

The reactor described in Examples 1 to 6 was charged with the following materials:
(i) 2,4,4,6-tetrachloro-2,5-cyclohexadienone: 0.23 g (0.001 mole);
(ii) phenolic compound: 0.010 mole;
(iii) reducing compound that is a chlorine acceptor: 0.0025 mole.

The procedure was as described for Examples 1 to 6. Duration of the experiments: 8 hours at 70° C.

Table IV below reflects the nature of the phenolic compound and of the reducing compound used, as well as the results of the analyses performed after the treatment.

TABLE IV

| EXPERIMENT | Phenolic compound reducing chlorine acceptor | % DC of the chlorocyclo-hexadienone | % YLD of 2,4,6-tri-chlorophenol | % YLD of 2,3,4,6-tetrachloro-phenol | Weight of chloro-phenoxy-phenols in g |
|---|---|---|---|---|---|
| Control C | 2,4,6-Trichlorophenol | 8 | — | 0 | 0 |
| Example 20 | Phenol Triphenylphosphine | 100 | 98.1 | 1.9 | 0 |
| Example 21 | Ortho-chlorophenol Triphenylphosphine | 100 | 91.8 | 0.3 | 0 |
| Example 22 | 2,4-Dichlorophenol Triphenylphosphine | 100 | 100 | 0 | 0 |
| Example 23 | Para-chlorophenol Thioanisole | 100 | 70.4 | 0 | 0 |
| Example 24 | 2,4,6-Trichlorophenol | — | 0 | 0 | 0 |

EXAMPLES 25 TO 31

The reactor described in Examples 1 to 6 was charged with the following materials:

(i) 2,3,4,4,6-pentachloro-2,5-cyclohexadienone: 0.265 g (0.001 mole);
(ii) phenolic compound: 0.010 mole;
(iii) reducing compound that is a chlorine acceptor: 0.0025 mole.

The procedure was as described in Examples 1 to 6. Duration of the experiments: 8 hours at 70° C.

Table V below reflects the nature of the phenolic compound and of the reducing compound used, as well as the results of the analyses performed after the treatment.

TABLE V

| EXPERIMENT | Phenolic compound reducing chlorine acceptor | % DC of the chlorocyclo-hexadienone | % YLD of 2,3,4,6-tetrachloro-phenol | % YLD of pentachloro-phenol | Weight of chloro-phenoxy-phenols in g |
|---|---|---|---|---|---|
| Example 25 | Phenol Triphenylphosphine | 100 | 96.1 | 0.1 | 0 |
| Example 26 | Ortho-chlorophenol Triphenylphosphine | 100 | 100 | 0.1 | 0 |
| Example 27 | Para-chlorophenol Triphenylphosphine | 100 | 100 | 0.1 | 0 |
| Example 28 | 2,4-Dichlorophenol Triphenylphosphine | 100 | 99.0 | 0 | 0 |
| Example 29 | 2,4,6-Trichlorophenol Triphenylphosphine | 100 | 82.4 | 0 | 0 |
| Example 30 | 2,3,4,6-Tetrachlorophenol Triphenylphosphine | 100 | — | 0 | 0 |
| Example 31 | 2,4,6-Trichlorophenol Triphenylphosphine | 100 | 99.1 | 0 | 0 |

EXAMPLES 32 TO 37

The reactor described in Examples 1 to 6 was charged with the following materials:
(i) 2,3,4,4,5,6-hexachloro-2,5-cyclohexadienone: 0.30 g (0.001 mole);
(ii) phenolic compound: 0.010 mole;
(iii) reducing compound that is a chlorine acceptor: 0.0025 mole.

The procedure was as described in Examples 1 to 6. duration of the experiments: 8 hours at 70° C.

Table VI below reflects the nature of the phenolic compound and of the reducing compound used, as well as the results of the analyses performed after the treatment.

EXAMPLES 38 TO 40

Treatment of a crude chlorination mixture

A three-necked flask equipped with a condenser, a central paddle-type stirrer and a dipping tube for the introduction of chlorine was charged with 100 g (613 mmol) of 2,4-dichlorophenol and 0.1 g of diisopropylamine. After the reaction mixture had been heated to 70° C., 15.2 liters (675 mmol) of Cl$_2$ were introduced over the course of 3 hours, 30 minutes. After the mixture was cooled, analysis by gas chromatography and by liquid chromatography equipped with UV and electrochemical double detection gave the following results:

2,4,4,6-tetrachlorocyclohexadienone:

1.5% ⟶ 7.9 mmol ⟶ YLD = 1.3%

2,4,6-trichlorophenol:

96.1% ⟶ 583.3 mmol ⟶ YLD = 96.8%

2,4-dichlorophenol:

0.05% ⟶ 0.4 mmol ⟶ DC = 99.9%

2,3,4,6-tetrachlorophenol:

1.4% ⟶ 7.4 mmol ⟶ YLD = 1.2%

TABLE VI

| EXPERIMENT | Phenolic compound Reducing chlorine acceptor | % DC of the chlorocyclo-hexadienone | % DC to pentachloro-phenol | Weight of chloro-phenoxy phenols in g |
|---|---|---|---|---|
| Control D | 2,4,6-Trichloro-phenol | 2 | 0 | 0 |
| Example 32 | Phenol Triphenylphosphine | 100 | 100 | 0 |
| Example 33 | Ortho-chlorophenol Triphenylphosphine | 100 | 100 | 0 |
| Example 34 | 2,6-Dichlorophenol Triphenylphosphine | 100 | 94.1 | 0 |
| Example 35 | 2,4-Dichlorophenol Triphenylphosphine | 100 | 97.0 | 0 |
| Example 36 | 2,3,4,6-Tetrachloro-phenol Triphenylphosphine | 100 | 96.0 | 0 |
| Example 37 | Pentachlorophenol Triphenylphosphine | 100 | — | 0 |

-continued

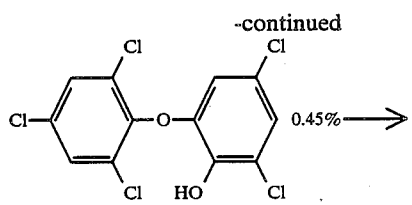

1.5 mmol ⟶ YLD = 0.5%

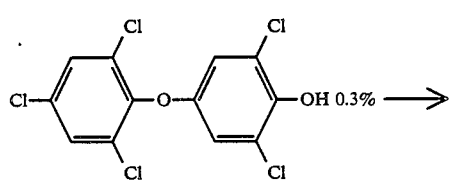

1 mmol ⟶ YLD = 0.3%

EXAMPLE 38

Treatment with triphenylphosphine

To 5.1 g of the reaction mass (0.33 mmol of tetrachlorocyclohexadienone), 0.2 g (0.64 mmol) of triphenylphosphine was added and the mixture was then heated for 1 hour, 30 minutes at 70° C. The solution rapidly decolorized during the heating. After it was cooled, 2,4,4,6-tetrachlorocyclohexadienone was no longer detected by analysis.

EXAMPLE 39

Treatment with hypophosphorous acid

To 5.1 g of the reaction mass (0.33 mmol of tetrachlorocyclohexadienone), 0.2 g (1.5 mmol) of 50% strength hypophosphorous acid was added; this mixture was heated for 96 hours at 70° C. After it was cooled, 2,4,4,6-tetrachlorocyclohexadienone was no longer detected.

EXAMPLE 40

Treatment with PCl$_3$

To 83.8 g of the crude reaction mass (5.4 mmol of 2,4,4,6-tetrachloro-2,5-cyclohexadienone), 3.35 g (24.4 mmol) of PCl$_3$ were added and the mixture was then heated to 70° C. for 1 hour, 20 minutes. After it was cooled, tetrachlorocyclohexadienone was no longer detected by analysis.

EXAMPLES 41 AND 42

The following materials were introduced into a 10-cm$^3$ glass flask equipped with a leakproof stopper:
(i) 2,4,4,6-tetrachloro-2,5-cyclohexadienone: 0.23 g (0.001 mole);
(ii) 2,4,6-trichlorophenol: 1.97 g (0.010 mole);
(iii) thiol: 0.0025 mole.

The mixture was heated to melting, and was then placed in an oven at 70° C. for 8 hours.

Using the analyses described in Examples 1 to 6, the following results were obtained:

| Example 41 with 2-mercaptoethanol (0.20 g): | |
|---|---|
| DC of 2,4,4,6-tetrachloro-2,5-cyclohexadienone: | 100% |
| YLD of phenoxyphenols: | 0% |

| Example 41 with 2-mercaptoethanol (0.20 g): | |
|---|---|
| YLD of 2,4,6-trichlorophenol: | 51.4% |

| Example 42 with 3,4-toluenedithiol (0.39 g): | |
|---|---|
| DC of 2,4,4,6-tetrachloro-2,5-cyclohexadienone: | 100% |
| YLD of phenoxyphenols: | 0% |
| YLD of 2,4,6-trichlorophenol: | 100% |

EXAMPLES 43 TO 45

The following materials were introduced into a 10-cm$^3$ glass flask equipped with a leakproof stopper:
(i) 2,4,4,6-tetrachloro-2,5-cyclohexadienone: 0.23 g (0.001 mole);
(ii) phenol: 0.94 g (0.010 mole);
(iii) thiol: 0.0025 mole.

The mixture was heated to melting, and was then placed in an oven at 70° C. for 8 hours.

The following results were obtained:

TABLE VII

| EXAMPLES | Thiol used | % DC of the 2,4,4,6-tetrachloro-2,5-cyclohexadienone | % YLD of 2,4,6-trichlorophenol |
|---|---|---|---|
| Example 43 | Thioacetic acid | 100 | 35.8 |
| Example 44 | 3-Methyl-2-propanethiol | 100 | 88.6 |
| Example 45 | Thiophenol | 100 | 31.2 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the stabilization of a mixture of chlorination of a phenol and/or a chlorophenol comprising stirring such mixture, which contains at least one unsaturated gem-dichlorinated cyclic ketone, in the presence of an effective stabilizing amount of at least one reducing compound that is a chlorine acceptor.

2. The process as defined by claim 1, said reducing compound that is a chlorine acceptor comprising an organic phosphite; a phosphine; a phosphinate; an arsine; an organic sulfide; a thiol; a thiocarboxylic acid; a mercapto acid; a metal hydride; a metal borohydride; a metal cyanoborohydride; an alkoxyborohydride; copper, tin, silver, cobalt, palladium, platinum, iridium, germanium or selenium, or derivative thereof; or a phenol, diphenol or triphenol.

3. The process as defined by claim 1, said reducing compound that is a chlorine acceptor comprising a trivalent phosphorus derivative of the general formula (I):

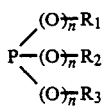

in which $R_1$, $R_2$ and $R_3$, which may be identical or different, are each a linear or branched chain alkyl radical having from 1 to 12 carbon atoms; a linear or branched chain alkyl radical having from 1 to 12 carbon atoms and containing one or more chlorine atoms; an alkyl radical containing one or more ether groups; a phenyl radical; a phenyl radical containing one or more chlorine atoms; a phenyl radical containing 1 or 2 alkyl substituents having 1 to 12 carbon atoms; a phenylalkyl radical, the aliphatic moiety of which contains 1 to 4 carbon atoms and in which the cyclic member optionally contains one or more chlorine atoms or 1 or 2 alkyl radicals having from 1 to 12 carbon atoms; or a cycloalkyl radical optionally substituted with one or more chlorine atoms or 1 or 2 alkyl radicals having from 1 to 12 carbon atoms; with the proviso that one or two of the radicals $R_1$, $R_2$ and $R_3$ can be a hydrogen atom; and the symbols n, which may be identical or different, are each 0 or 1.

4. The process as defined by claim 3, said trivalent phosphorus derivative of the formula (I) comprising triphenyl phosphite, a tris(chlorophenyl) phosphite, a tris(dichlorophenyl) phosphite, a tris(trichlorophenyl) phosphite, trimethyl phosphite, triethyl phosphite, tributyl phosphite, trioctyl phosphite, a tris(nonylphenyl) phosphite, tris(2,4-di-tert-butylphenyl) phosphite, tribenzyl phosphite, tris(phenethyl) phosphite, methyl diphenylphosphinate, tris(2-ethoxyethyl) phosphite, tricyclohexyl phosphite, triphenylphosphine, diphenylmethylphosphine, diphenylethylphosphine, diethylphenylphosphine or tributylphosphine.

5. The process as defined by claim 1, said reducing compound that is a chlorine acceptor comprising an organic sulfide of the general formula (II):

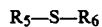 (II)

in which $R_5$ and $R_6$, which may be identical or different, are each a phenyl radical optionally substituted with one or more alkyl, alkoxy or hydroxyl radicals or chlorine atoms; an alkyl radical; a phenylalkyl radical optionally substituted with one or more alkyl, alkoxy or hydroxyl radicals or chlorine atoms; or a cyclopentyl or cyclohexyl radical optionally substituted with one or more alkyl, alkoxy or hydroxyl radicals or chlorine atoms.

6. The process as defined by claim 5, said reducing compound that is a chlorine acceptor comprising thioanisole, diphenyl sulfide, phenyl 4-chlorophenyl sulfide, bis(4-chlorophenyl) sulfide, bis(2-hydroxy-4,6-di-tert-butylphenyl) sulfide, bis(4-hydroxy-3,5-dimethylphenyl) sulfide, bis(2-hydroxy-3,5-di-tert-butylphenyl) sulfide, phenyl cyclohexyl sulfide, phenyl butyl sulfide, 4-chlorophenyl hexyl sulfide, 4-methylphenyl dodecyl sulfide, benzyl octyl sulfide, 4-methoxyphenyl ethyl sulfide, phenyl stearyl sulfide, dihexyl sulfide, ethyl hexyl sulfide, dioctyl sulfide, propyl 4-methylcyclohexyl sulfide or methyl 4-chlorocyclohexyl sulfide.

7. The process as defined by claim 6, said reducing compound that is a chlorine acceptor comprising thioanisole.

8. The process as defined by claim 1, said reducing compound that is a chlorine acceptor comprising a thiol, mercapto acid or thiocarboxylic acid of the general formula (III):

 (III)

in which $R_7$ is a linear or branched chain alkyl radical optionally substituted with one or more OH groups, —COOH groups or chlorine atoms, or such radical containing one or more oxygen atoms —O— along the chain thereof; a phenyl radical optionally substituted with one or more alkyl, alkoxy, hydroxyl or carboxyl radicals or chlorine atoms; a phenylalkyl radical optionally substituted with one or more alkyl, alkoxy, hydroxyl or carboxyl radicals or chlorine atoms; a cyclopentyl or cyclohexyl radical optionally substituted with one or more alkyl, alkoxy, hydroxyl or carboxyl radicals or chlorine atoms; or a radical $R_7$—CO—, in which $R_7$ is as defined above.

9. The process as defined by claim 8, said reducing compound that is a chlorine acceptor comprising 2-mercaptoethanol, 3,4-toluenedithiol, 2-methyl-2-propanethiol, thiophenol, thioacetic acid, thioglycolic acid or 2-mercaptosuccinic acid.

10. The process as defined by claim 1, said reducing compound that is a chlorine acceptor comprising a hydride of an alkali metal, of an alkaline earth metal or of aluminum and an alkali metal, an alkali metal borohydride, an alkali metal cyanoborohydride or an alkali metal alkoxyborohydride.

11. The process as defined by claim 10, said reducing compound that is a chlorine acceptor comprising sodium hydride, potassium hydride, lithium hydride, calcium hydride, magnesium hydride, lithium aluminum hydride, sodium borohydride, potassium borohydride, sodium cyanoborohydride, potassium cyanoborohydride, sodium trimethoxyborohydride, sodium triethoxyborohydride, potassium trimethoxyborohydride, potassium triethoxyborohydride or sodium dimethoxyborohydride.

12. The process as defined by claim 1, said reducing compound that is a chlorine acceptor comprising copper, stannous chloride or ruthenium trichloride.

13. The process as defined by claim 1, said reducing compound that is a chlorine acceptor comprising a phenol, diphenol or triphenol optionally containing one or more alkyl or alkoxy substituents having from 1 to 4 carbon atoms.

14. The process as defined by claim 13, said reducing compound that is a chlorine acceptor comprising phenol, 2-methylphenol, 3-methylphenol, 4-methylphenol, 2-methoxyphenol, 3-methoxyphenol, 4-methoxyphenol, 2-ethoxyphenol, 3-ethoxyphenol, 4-ethoxyphenol, 4-tert-butylphenol, pyrocatechol, resorcinol, hydroquinone, 2-methylhydroquinone, 2-methoxyhydroquinone, 4-methoxypyrocatechol, 2,6-dimethoxyhydroquinone, 1-naphthol, 2-naphthol, 1,2-dihydroxynaphthalene, 1,3-dihydroxynaphthalene, 1,4-dihydroxynaphthalene, 1,5-dihydroxynaphthalene, 1,6-dihydroxynaphthalene, 1,7-dihydroxynaphthalene, 1,8-dihydroxynaphthalene, 2,3-dihydroxynaphthalene, 2,6-dihydroxynaphthalene, 2,7-dihydroxynaphthalene, pyrogallol, phloroglucinol, hydroxyquinol, 2-chlorohydroquinone or vitamin E.

15. The process as defined by claim 1, comprising introducing phosphorus trichloride, phosphorous acid or hypophosphorous acid into the mixture of chlorination.

16. The process as defined by claim 1, said stirring being carried out at a temperature of from 20° C. to 200° C.

17. The process as defined by claim 16, said stirring being carried out at a temperature of from 60° C. to 150° C.

18. The process as defined by claim 1, wherein the molar amount of the reducing compound that is a chlorine acceptor is at least equal to the molar amount of unsaturated gem-dichlorinated cyclic ketones in the mixture.

19. The product of the process as defined by claim 1.

20. The process as defined by claim 1, wherein said unsaturated gem-dichlorinated cyclic ketone comprises a gem-dichlorinated cyclohexadienone containing 1, 2, 3 or 4 other chlorine atoms on different carbon atoms of the ring.

21. The process as defined by claim 1, wherein said unsaturated gem-dichlorinated cyclic ketone comprises a gem-dichlorinated cyclohexenone containing 1, 2, 3, 4, 5 or 6 other chlorine atoms on different carbon atoms of the ring.

22. The process as defined by claim 20, wherein said cyclohexadienone comprises 4,4-dichloro-2,5-cyclohexadienones or 6,6-dichloro-2,4-cyclohexadienones containing, in addition, 1, 2, 3 or 4 chlorine atoms.

23. The process as defined by claim 21, wherein said cyclohexenone comprises 2,2-dichloro-3-cyclohexenones; 6,6-dichloro-2-cyclohexenones; 4,4-dichloro-2-cyclohexenones or 6,6-dichloro-3-cyclohexenones containing, in addition, 1, 2, 3, 4, 5 or 6 chlorine atoms.

24. The process as defined by claim 22, wherein said cyclohexadienone comprises:
6,6-dichloro-2,4-cyclohexadienone,
4,4-dichloro-2,5-cyclohexadienone,
2,4,4,6-tetrachloro-2,5-cyclohexadienone,
2,4,6,6-tetrachloro-2,4-cyclohexadienone,
2,3,4,4,6-pentachloro-2,5-cyclohexadienone,
2,4,5,6,6-pentachloro-2,4-cyclohexadienone,
2,3,4,6,6-pentachloro-2,4-cyclohexadienone,
2,3,4,4,5,6-hexachloro-2,5-cyclohexadienone, or
2,3,4,5,6,6-hexachloro-2,4-cyclohexadienone.

25. The process as defined by claim 23, wherein said cyclohexenone comprises:
2,4,5,6,6-pentachloro-2-cyclohexenone,
2,4,4,5,6,6-hexachloro-2-cyclohexenone,
2,2,4,5,6,6-hexachloro-3-cyclohexenone,
2,4,4,5,5,6,6-heptachloro-2-cyclohexenone,
2,2,3,4,5,6,6-heptachloro-3-cyclohexenone,
2,3,4,4,5,5,6-heptachloro-2-cyclohexenone,
2,3,4,4,5,6,6-heptachloro-2-cyclohexenone,
2,3,4,4,5,5,6,6-octachloro-2-cyclohexenone, or
2,2,3,4,5,5,6,6-octachloro-3-cyclohexenone.

26. A process for the stabilization of a mixture of chlorination of a phenol and/or a chlorophenol comprising:
chlorinating a phenol, monochlorophenol or dichlorophenol to produce a trichlorophenol, tetrachlorophenol or pentachlorophenol mixture; and stirring said mixture comprising at least one unsaturated gem-dichlorinated cyclic ketone in the presence of an effective stabilizing amount of at least one reducing compound that is a chlorine acceptor.

* * * * *